US008182837B2

(12) United States Patent
Smith

(10) Patent No.: US 8,182,837 B2
(45) Date of Patent: *May 22, 2012

(54) METHODS AND COMPOSITIONS FOR REDUCING THE RISK ASSOCIATED WITH THE ADMINISTRATION OF OPIOID ANALGESICS IN PATIENTS WITH DIAGNOSED OR UNDIAGNOSED RESPIRATORY ILLNESS

(75) Inventor: Maree T. Smith, Bardon (AU)

(73) Assignee: QRxPharma Limited, North Sydney (AU)

(*) Notice: Subject to any disclaimer, the term of this patent is extended or adjusted under 35 U.S.C. 154(b) by 137 days.

This patent is subject to a terminal disclaimer.

(21) Appl. No.: 11/544,187

(22) Filed: Oct. 6, 2006

(65) Prior Publication Data

US 2007/0031489 A1    Feb. 8, 2007

Related U.S. Application Data

(62) Division of application No. 10/661,458, filed on Sep. 10, 2003, now abandoned.

(51) Int. Cl.
*A61K 31/485* (2006.01)
*A61K 31/445* (2006.01)
*A61K 9/20* (2006.01)

(52) U.S. Cl. .................. 424/464; 514/282; 514/317
(58) Field of Classification Search .................. None
See application file for complete search history.

(56) References Cited

U.S. PATENT DOCUMENTS

| 4,522,811 | A | 6/1985 | Eppstein et al. |
| 5,317,022 | A | 5/1994 | Borsodi et al. |
| 5,457,110 | A | 10/1995 | Borsodi et al. |
| 5,508,042 | A | 4/1996 | Oshlack et al. |
| 5,549,912 | A | 8/1996 | Oshlack et al. |
| 6,310,072 | B1* | 10/2001 | Smith et al. ........... 514/282 |
| 2005/0053656 | A1 | 3/2005 | Ping |
| 2005/0053659 | A1 | 3/2005 | Pace et al. |
| 2008/0039463 | A1 | 2/2008 | Nadeson et al. |
| 2009/0291975 | A1 | 11/2009 | Stern et al. |

FOREIGN PATENT DOCUMENTS

| AU | 706691 B | 5/1997 |
| EP | 1667723 | 6/2006 |
| JP | 2007-505139 A | 3/2007 |
| WO | WO 96/16063 A1 | 5/1996 |
| WO | WO 97/14438 * | 4/1997 |
| WO | WO 2005/025621 A1 | 3/2005 |

OTHER PUBLICATIONS

Ross et al. (Pain 2000, 84, 421-428).*
Riley et al. (Otolaryngol Head Neck Surg 1997, 117, 648-52).*
Office Action Issued Against U.S. Appl. No. 10/661,458, pp. 1-11, May 28, 2008.
Office Action Issued Against U.S. Appl. No. 10/661,458, pp. 1-12, Apr. 15, 2009.
Beaver et al., Analgesic Studies of Codeine and Oxycodone in Patients with Cancer. I. Comparisons of Oral with Intramuscular Codeine and of Oral with Intramuscular Oxycodone, *The Journal of Pharmacology and Experimental Therapeutics*, vol. 207, pp. 92-100, Jan. 1, 1978.
Bolan et al., Synergy Between Mu Opioid Ligands: Evidence for Functional Interactions Among Mu Opioid Receptor Subtypes, *J of Pharmacol. and Exp. Therapuetics*, vol. 303 (2), pp. 557-562, Nov. 1, 2002.
Cherny et al., Chapter 81: Practical Issues in the Management of Cancer Pain, *Textbook of Cancer Pain*, 3rd ed., pp. 1437-1467, Jan. 1, 1994.
Combes et al., The Effects of Residual Pain on Oxygenation and Breathing Pattern During Morphine Analgesia, *Anesth. Analg.*, vol. 90, pp. 156-160, Jan. 1, 2000.
Connor et al., µ-Opioid Receptor Desensitization: Is Morphine Different?, *British Journal of Pharmacology*, vol. 143, pp. 685-696, Jan. 1, 2004.
Du Bose et al., Respiratory Effects of Opioids, *International Association for the Study of Pain Newsletter*, pp. 1-6, Jul. 1, 1997.
Grach et al., Can Coadministration of Oxycodone and Morphine Produce Analgesic Synergy in Humans? An Experimental Cold Pain Study, *British Journal of Clinical Pharmacology*, vol. 58 (3), pp. 235-242, Jan. 1, 2004.
Gutstein et al., Chapter 23: Opioid Analgesics, *The Pharmacological Basis of Therapeutics*, 10th Ed., pp. 569-619, Jan. 1, 1980.
Heiskanen et al., Controlled-Release Oxycodone and Morphine in Cancer Related Pain, *Pain*, vol. 73, pp. 37-45, Jan. 1, 1997.
Kalso et al., Intravenous Morphine and Oxycodone for Pain After Abdominal Surgery, *Acta Anaesthesiologica Scandinavica*, vol. 35, pp. 642-646, Jan. 1, 1991.
Korttila et al., Buprenorphine as Premedication and as Analgesic During and After Light Isoflurane-N2O-O2 Anaesthesia. A Comparison with Oxycodone Plus Fentanyl, *Acta Anaesthesiologica Scandinavica*, vol. 31, pp. 673-679, Nov. 1, 1987.
Mercer, M., Anaesthesia for the Patient with Respiratory Disease, *Practical Procedures*, vol. 12, pp. 1-15, Jan. 1, 2000. Osei-Gyimah et al., Synthesis and Analgesic Activity of Some 14 Beta-Substituted Analogues of Morphine, *J Med Chem*, vol. 23 (2), pp. 1, Feb. 1, 1980.
Raehal et al., Mu Opioid Receptor Regulation and Opiate Responsiveness, *The AAPS Journal*, vol. 7 (3), pp. E587-E591, Oct. 19, 2005.
Reid et al., Oxycodone for Cancer-Related Pain, *Arch Intern Med*, vol. 166, pp. 837-843, Apr. 24, 2006.
Ross et al., The Intrinsic Antinociceptive Effects of Oxycodone Appear to be Kappa-Opioid Receptor Mediated, *Pain*, vol. 73 (2), pp. 151-157, Nov. 1, 1997.

(Continued)

*Primary Examiner* — Ernst Arnold

(74) *Attorney, Agent, or Firm* — Frommer Lawrence & Haug LLP; Sandra Kuzmich, Esq.; Russell A. Garman

(57) ABSTRACT

The present invention relates to methods for reducing the risk associated with the administration of opioid analgesics in patients diagnosed or undiagnosed with respiratory illness by administering an analgesic composition comprising a sub-analgesic dosage of a µ-opioid agonist selected from the group consisting of morphine, fentanyl, sufentanil, alfentanil, oxymorphone and hydromorphone, or a pharmaceutically acceptable salt thereof, and a sub-analgesic dosage of oxycodone which is a $\kappa_2$-opioid agonist or a pharmaceutically acceptable salt thereof.

16 Claims, 1 Drawing Sheet

OTHER PUBLICATIONS

Smith et al., Neuroexcitatory Effects of Morphine and Hydromorphone: Evidence Implicating the 3-glucuronide Metabolites, *Clin. Exp. Pharmacol. Physiol.*, vol. 27 (7), pp. 524-528, Jul. 1, 2000.

Twycross, R. G., Chapter 49: Opioids, *Textbook of Cancer Pain*, 3rd ed., pp. 943-962, Jan. 1, 1994.

Wilson, P., Complications of Opiate Pharmacotherapy, *Seminars in Pain Medicine*, vol. 2, pp. 228-232, Dec. 1, 2004.

Office Action dated Dec. 28, 2011, in relation to U.S. Appl. No. 12/881,677.

Amendment and Response to Office Action and Record of Interviews filed Jan. 28, 2011, in relation to U.S. Appl. No. 12/881,677.

Office Action dated Dec. 28, 2011, in relation to U.S. Appl. No. 12/881,728.

Amendment and Response to Office Action and Record of Interviews filed Jan. 28, 2011, in relation to U.S. Appl. No. 12/881,728.

Bruera et al. Randomized, double-blind, cross-over trial comparing safety and efficacy of oral controlled-release oxycodone with controlled-release morphine in patients with cancer pain. *Journal of Clinical Oncology*, 1998, 16(10): 3222-29.

Non-final Office Action issued on May 13, 2010 for U.S. Appl. No. 12/469,438, pp. 1-22.

Heiskanen et al. Controlled-release oxycodone and morphine in cancer related pain. *Pain*, 1997, 73: 37-45.

Foley. The treatment of cancer pain. *New England Journal of Medicine*, 1985, 313: 84-95.

Levy. Pharmacological treatment of cancer pain. *New England Journal of Medicine*, 1996, 335: 1124-1132.

Yudofsky et al., The American Psychiatric Publishing Textbook of Neuropsychiatry and Behavioral Neurosciences, American Psychiatric Publishing, Inc., Arlington, VA, Edition 5, 2008, p. 388.

Jolly et al., Cancer Pain Management, Fisch MJ and Burton AW, eds., McGraw-Hill Companies, New York, 2006, 308.

U.S. Appl. No. 12/567,209, filed Sep. 25, 2009, Stern et al.

U.S. Appl. No. 12/579,173, filed Oct. 14, 2009, Stern et al.

Grach et al., Can Coadministration of Oxycodone and Morphine Produce Analgesic Synergy in Humans? An Experimental Cold Pain Study, Brit. J. Clin. Pharmacol., 58(3), 2004, 235-242.

Smith et al., Co-administration of Oxycodone and Morphine and Analgesic Synergy Re-Examined, Brit. J. Clin. Pharmacol., 59(4), 2005, 486-487.

Grach et al., Response to Smith MT and de la Iglesia FA: 'Coadministration of Oxycodone and Morphine and Analgesic Synergy Re-Examined', Brit. J. Clin. Pharmacol., 59(4), 2005, 487-488.

Campora et al., J. Pain Symptom Manage., 6, 1991, 428-30).

Coyle et al., Cancer Pain Management, 2nd Ed., McGuire DB, Yarbro CH and Ferrell BR, eds., Jones and Bartlett Publishers Inc., Massachusetts, 1995, 113.

Office Action Issued Against U.S. Appl. No. 10/661,458, pp. 1-14, Oct. 28, 2009.

International Search Report for Application No. PCT/US09/62917, pp. 1-4, Dec. 30, 2009.

Mercadante et al., Rapid Titration with Intravenous Morphine for Severe Cancer Pain and Immediate Oral Conversion, Cancer, vol. 95 (1), pp. 201-208, Jan. 1, 2002.

\* cited by examiner

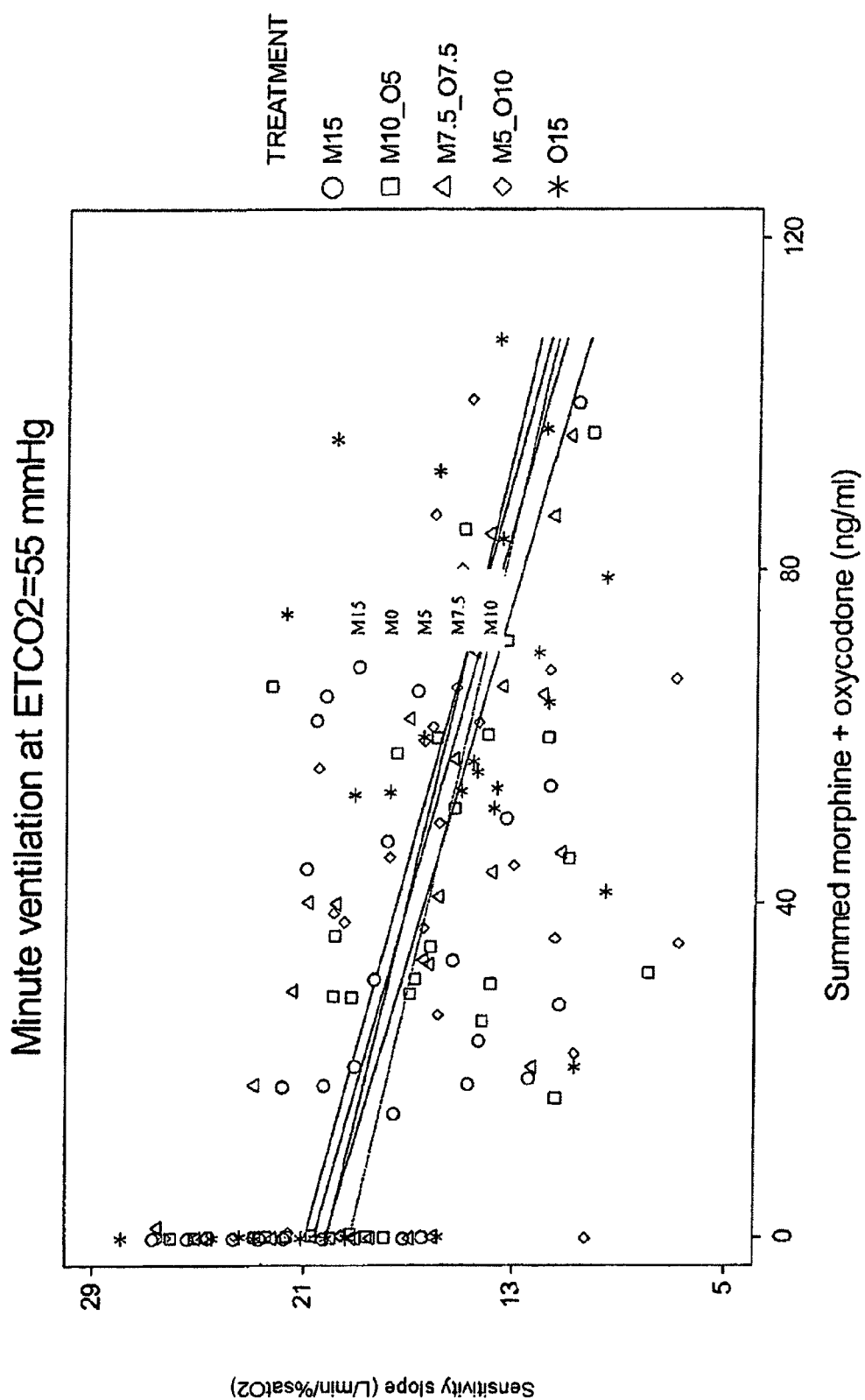

METHODS AND COMPOSITIONS FOR REDUCING THE RISK ASSOCIATED WITH THE ADMINISTRATION OF OPIOID ANALGESICS IN PATIENTS WITH DIAGNOSED OR UNDIAGNOSED RESPIRATORY ILLNESS

CROSS REFERENCE TO RELATED APPLICATIONS

This application is a divisional of U.S. patent application Ser. No. 10/661,458 filed Sep. 10, 2003.

FIELD OF THE INVENTION

The technical field of the invention relates to the use of sub-analgesic doses of opioids for the treatment of pain in patients with a diagnosed or undiagnosed respiratory illness or respiratory disorder.

BACKGROUND OF THE INVENTION

When a patient experiences significant pain as the result of a serious traumatic injury, a surgical procedure, or chronic illness (e.g., cancer), relief requires strong medication under a doctor's prescription. Opiate drugs are a class of pain-relieving prescription drugs frequently prescribed for moderate to severe pain. The opioids are a group of drugs, both natural and synthetic, that are employed primarily as centrally-acting analgesics and are opium or morphine-like in their properties (Gilman et al., 1980, GOODMAN AND GILMAN'S THE PHARMACOLOGICAL BASIS OF THERAPEUTICS, Chapter 24:494-534, Pergamon Press; hereby incorporated by reference). The opioids include morphine and morphine-like homologs, including, e.g., the semisynthetic derivatives codeine (methylmorphine) and hydrocodone (dihydrocodeinone), among many other such derivatives. Morphine and related opioids exhibit agonist activity in the central nervous system (CNS) (referring to the brain and spinal cord) at μ (mu) opioid receptors, as well as showing affinity for the δ (delta) and κ (kappa) opioid receptors, to produce a range of effects including analgesia, drowsiness, and changes in mood, among others. In addition to potent analgesic effects, the morphine-related opioids may also use a number of undesirable effects, including, for example, nausea, vomiting, dizziness, mental clouding, dysphoria, pruritus, constipation, increased biliary tract pressure, urinary retention, hypotension and, most notably, respiratory depression.

Opioids depress all phases of respiratory activity to some extent. Respiratory depression becomes significant when it leads to the need for medical intervention. Opioids interfere with carbon dioxide chemoreceptors in the medulla leading to increased retention of carbon dioxide. The increase in carbon dioxide levels does not stimulate a concomitant increase in respiratory rate; thus, the body is forced to rely on a less sensitive oxygen-driven respiration-regulating mechanism. Respiratory depression may be treated by artificial ventilation or be reversed by administration of chemical agents such as naloxone. Naloxone will immediately reverse opioid-induced respiratory depression, but the dose may have to be repeated due to the short duration of action of naloxone. More importantly, naloxone will also antagonise the analgesic effect, thus negating the primary clinical purpose of administration of the opioid.

Patients with respiratory illness, whether diagnosed or undiagnosed, represent a significant subpopulation of patients requiring pain management with opiates for reasons unrelated to their respiratory illness. Patients with compromised lungs (i.e., with respiratory illnesses) are at increased risk for opiate induced respiratory depression and/or cessation because of their impaired respiratory capability. Respiratory depression is a decrease in the rate or depth of respiratory effort and a resulting decrease in level of alertness.

Respiratory illnesses with increased susceptibility to opiate-induced respiratory depression and/or cessation include infectious or inflammatory conditions such as asthma, bronchiectasis, pulmonary tuberculosis, chronic obstructive pulmonary disease, bronchitis, bronchopneumonia, chronic laryngitis, chronic sinusitis, emphysema, fibrosing alveolitis, idiopathic pulmonary fibrosis and sarcoidosis. Neoplastic diseases of the lung also are included, for example, non-small cell lung cancer, adenocarcinoma, squamous cell carcinoma, large cell carcinoma, undifferentiated carcinoma, small cell lung cancer, oat cell cancer and mesothelioma Du Bose and Berde (Technical Corner, *International Association for the Study of Pain Newsletter*, July/August, 1997) provide a number of specific examples of the importance of respiratory depression in patient groups as follows. Respiratory depression can occur in circumstances where the duration of an opioid's analgesic and respiratory depressant effects outlasts the duration of a painful stimulus. For example, a burn dressing change or a bone marrow aspiration may be intensely painful for only a brief time. An opioid such as morphine, which has comparatively slow onset and prolonged duration, may be titrated to give an appropriate degree of analgesia and sedation. However, excessive sedation and respiratory depression may occur following the procedure when respiratory stimulation declines along with a rapid reduction in the intensity of pain and distress. This complication can be prevented in most circumstances by constant observation, awakening the patient, and encouraging deep breathing until the opioid's effects dissipate. Even modest doses of opioids in awake subjects can have dramatic effects on the ventilatory response to hypoxemia. While depression of ventilatory responses to hypoxemia is of little consequence to most healthy subjects, the consequences can be severe in patients who may be dependent on hypoxic respiratory drive, such as those with chronic obstructive pulmonary disease (COPD) and long-standing hypercapnia. Also, certain disease states may increase respiratory risks from the administration of opioids. For example, disorders of neural tube development, including spina bifida, can be associated with abnormal respiratory control, even in patients with mild degrees of neurologic impairment. The use of opioids in these high-risk groups may require more judicious dose titration and closer observation. Morbidly obese and Pickwickian patients may have difficulties with opioid dose titration. Patient-controlled analgesia (PCA) use in obese postoperative patients showed as much as a 10-fold difference in opiate requirements.

DuBose and Berde (ibid.) further note that while pain antagonizes opioid-induced respiratory depression, sleep can intensify the depressant effects of opioids. During normal respiration, subatmospheric pressure in the pharynx tends to draw the tongue against the palate, narrowing the airway. The finely coordinated contraction of the tongue (especially the genioglossus) and pharyngeal musculature helps to maintain airway patency and prevent snoring or inspiratory collapse of the airway. Sleep and opioids separately, and in concert, depress genioglossus and pharyngeal muscle tone and diminish airway protective reflexes. Critical incidents from opioid-induced respiratory depression appear to be more common in the hours from midnight to 6 a.m., which is of more critical importance due to the lessened level of scrutiny of possibly affected patients during night time hours.

Depression of level of consciousness is an extremely useful guide to observing clinical effect in patients receiving opioids. Respiratory depression is almost always preceded by sedation or clouded sensorium. It has also been noted that abdominal surgery is associated with postoperative sleep disturbance. Also sleep disturbance and episodic hypoxemia are extremely common in patients receiving opioids following surgery. REM sleep is typically suppressed initially, and then a rebound increase in REM sleep often occurs on the second and third postoperative nights. It has been suggested that opioids contribute to disturbed sleep postoperatively.

Perhaps the respiratory illnesses presenting the greatest concern are those conditions which, by definition, involve a major defect in respiratory control, most particularly in sleep disordered breathing such as sleep apnea syndrome (SAS).

Sleep apnea syndrome (SAS) is a breathing disorder characterized by apneas and hypopneas. Apneas are a cessation of airflow for ten seconds or more and hypopnea: a decrease in flow by at least 50% for 10 seconds or more. Both apneas and hypopneas are associated with sleep arousal and/or oxygen desaturations of 3% or more. Apneas and hypopneas result from upper airway occlusion, either full or partial, or from a loss of or a significant decrease in the autonomic drive to breathe. There are three types of apnea: obstructive, central, and mixed. Obstructive sleep apnea (OSA) is the most common type of sleep apnea. OSA occurs when the upper airway occludes (either partially or fully) but efforts to breathe continue. The primary causes of upper airway obstruction are lack of muscle tone during sleep, excess tissue in the upper airway, and anatomic abnormalities in the upper airway and jaw. Central sleep apnea (CSA) affects only 5-10% of the sleep apnea population. CSA occurs when both airflow and respiratory effort cease. This cessation of breathing results from a loss of the autonomic drive to breathe. Mixed apneas occur when an initial central component followed by an obstructive component causes a cessation of breathing. In the absence of formal sleep studies, the diagnosis can be made clinically by interviewing patients and their sleeping partners. Clinical signs include loud snoring, observed apneic episodes, and excessive daytime somnolence.

The cause of upper airway obstruction in SAS patients was long thought to be the tongue, but fluoroscopy during sleep has shown this is rarely the case. The oropharynx itself is the most collapsible segment of the upper airway and the most likely site of obstruction. Physiologic studies have demonstrated that patients with SAS have narrowed upper airways to start with, so they are more susceptible than other patients to drugs or anesthetics that suppress pharyngeal muscle tone.

In normal, awake patients, there is a phasic activity of the pharyngeal muscles that contracts them immediately before inspiration, helping to resist the negative pressure generated by the diaphragm and keeping the airway from collapsing. This phasic pharyngeal contraction is markedly reduced both by REM sleep and by opiate administration. Patients with sleep apnea appear to be much more sensitive than normal individuals, even to minimal levels of sedation. The increased sensitivity of their hypoglossal nerves to low doses of anesthesia has been well described.

This increased tendency to airway obstruction can occur out of proportion to the level of sedation the opiates achieve. This would explain why many of the patients complained of significant pain shortly before falling asleep and developing obstructive episodes. Apneic episodes can occur with all routes of opioid administration. This increased sensitivity of SAS patients to opiates may be impossible to reverse with antagonists. One well-documented case in the literature described an obese patient who became comatose after a minimal dose of meperidine given intramuscularly as a premedication. Neither the airway obstruction nor the obtundation could be satisfactorily reversed with naloxone. When the patient had spontaneously recovered, his physicians ordered a sleep study, which confirmed the diagnosis of sleep apnea. This patient had a documented decrease in arterial pot to 30 mm Hg spontaneously during sleep associated with multiple PVC's and episodes of sinus bradycardia. Had this not been noticed intraoperatively, it might have happened unmonitored on the ward.

On a daily basis, surgical patients are wheeled into operating rooms with unrecognized obstructive sleep apnea (OSA). Diagnosed OSA patients, as well as undiagnosed patients who present with classic signs and symptoms, are at risk for significant post-operative respiratory complications after receiving a general anesthetic and postoperative opiate analgesia. Yet health care providers frequently fail to screen for OSA, and when it is suspected or diagnosed, often fail to incorporate this information into the perioperative plan of care. Approximately 9% of women and 24% of men ages 30 to 60 have apnea/hypopnea episodes. Additionally, it has been estimated that 80% to 90% of patients with OSA are undiagnosed.

The administration of opiate pain medication in patients with sleep apnea syndrome must be closely monitored. One problem observed by physicians was that pain medication orders for any given patient might be written by different individuals (surgeon, anesthesiologist, or primary care practitioner), not all of whom may be aware of the diagnosis of OSA. Clearly, wider understanding of this syndrome is crucial, and suggestions included red-flagging the charts of these patients to warn of the risks of opiate usage.

Farney et al. (*Chest* 203: 632-639 (2003)) described three patients who illustrate distinctive patterns of sleep-disordered breathing who are receiving long-term, sustained-release opioid medications. Polysomnography shows respiratory disturbances occur predominantly during non-rapid eye movement (NREM) sleep and are characterized by ataxic breathing, central apneas, sustained hypoxemia, and unusually prolonged obstructive "hypopneas" secondary to delayed arousal responses. In contrast to what is usually observed in subjects with obstructive sleep apnea (OSA), oxygen desaturation is more severe and respiratory disturbances are longer during NREM sleep compared to rapid eye movement sleep. Further they noted that is these patients treatment with a nasal CPAP (continuous positive airway pressure) device without supplemental oxygen was ineffective. They conclude that opioids could interfere with providing effective nasal CPAP treatment and that there is potential for harm because patients with OSA syndrome continue to be under-diagnosed while at the same time the use of opioids for chronic pain control continues to increase.

As pain is treated more aggressively, the tragic complication of respiratory arrest in patients with sleep apnea syndrome and other respiratory illnesses may be seen more frequently.

At present, it is impossible to imagine major postoperative and post-traumatic pain relief without opioid therapy. It would be highly desirable if therapies were available that provided adequate and satisfactory pain relief with a minimum of respiratory risk in inducing severe respiratory depression, episodes of sleep apnea and/or complete cessation of respiration.

SUMMARY OF THE INVENTION

The present invention, in a first embodiment, provides a method for reducing the risk associated with the administration of opioid analgesics in patients with diagnosed or undiagnosed respiratory illness, or at risk for same, by administering an analgesic composition comprising a sub-analgesic dosage of a p-opioid agonist selected from the group consisting of morphine, fentanyl, sufentanil, alfentanil, oxymorphone and hydromorphone, or a pharmaceutically acceptable salt thereof, and a sub-analgesic dosage of oxycodone, a $\kappa_2$-opioid agonist, or a pharmaceutically acceptable salt thereof, wherein the method achieves an analgesic effect in the patient to which the composition is administered. Alternatively, this embodiment of the present invention contemplates a p-opioid agonist in the form of a pharmaceutically acceptable salt. Preferably, the p-opioid agonist is morphine. Alternatively, the p-opioid agonist is fentanyl. In yet another alternative, the p-opioid agonist is hydromorphone. In an alternative embodiment, the oxycodone is in the form of a pharmaceutically acceptable salt.

Also contemplated by the present invention is use of a composition wherein the combined mass of morphine and oxycodone is about 50% of the mass of morphine alone required to achieve the same analgesic effect in the patient to which the composition is administered. In an alternative embodiment, the present invention contemplates administration of a composition wherein the combined mass of morphine and oxycodone is about 75% of the mass of oxycodone alone required to achieve the same analgesic effect in the patient to which the composition is administered.

The method of the present invention encompasses a composition that is administered in an immediate release oral dosage form or, alternatively, is administered in a sustained release oral dosage form. Alternatively, the composition used in the practice of the present invention may be administered through a subcutaneous, intravenous, intramuscular, epidural, transdermal, inhalation, buccal or sublingual route.

In another aspect, the present invention contemplates a respiratory illness selected from the group consisting of asthma, bronchiectasis, pulmonary tuberculosis, chronic obstructive pulmonary disease, bronchitis, bronchopneumonia, chronic laryngitis, chronic sinusitis, emphysema, fibrosing alveolitis, idiopathic pulmonary fibrosis and sarcoidosis.

In an alternative aspect, the present invention contemplates a respiratory illness that is cancer. The cancer may be lung cancer. The cancer may be non-small cell lung cancer, adenocarcinoma, squamous cell carcinoma, large cell carcinoma, undifferentiated carcinoma, small cell lung cancer, oat cell cancer and mesothelioma.

The method of the present invention also contemplates the clinical situation where the respiratory illness is a respiratory sleep disorder. It is possible that the respiratory sleep disorder is a sleep apnea, selected from the group consisting of central sleep apnea, obstructive sleep apnea and mixed sleep apnea.

In yet another embodiment, the present invention provides a method of minimizing the risk of developing sleep apnea in susceptible patients treated for the alleviation or prevention of pain, wherein the method comprises the step of administering an analgesic composition comprising a sub-analgesic dosage of a p-opioid agonist selected from the group consisting of morphine, fentanyl, sufentanil, alfentanil, oxymorphone and hydromorphone, or a pharmaceutically acceptable salt thereof, and a sub-analgesic dosage of oxycodone, a $\kappa_2$-opioid agonist, or a pharmaceutically acceptable salt thereof. The sleep apnea may be selected from the group consisting of central sleep apnea, obstructive sleep apnea and mixed sleep apnea.

BRIEF DESCRIPTION OF THE DRAWINGS

FIG. 1 illustrates the effect of morphine and oxycodone plasma concentrations on minute ventilation.

DETAILED DESCRIPTION OF THE INVENTION

The present invention relates to methods for reducing the risk associated with the administration of opioid analgesics in patients diagnosed or undiagnosed with respiratory illness by administering an analgesic composition comprising a sub-analgesic dosage of a p-opioid agonist selected from the group consisting of morphine, fentanyl, sufentanil, alfentanil, oxymorphone and hydromorphone, or a pharmaceutically acceptable salt thereof, and a sub-analgesic dosage of oxycodone which is a K2-opioid agonist or a pharmaceutically acceptable salt thereof.

According to one aspect of the invention there is provided an analgesic composition, for use in the methods of the present invention, comprising a sub-analgesic dosage of a p-opioid agonist suitably in the form of a pharmaceutically acceptable salt and a sub-analgesic dosage of a k2-opioid agonist suitably in the form of a pharmaceutically acceptable salt.

The term "p-opioid agonist" as used herein refers to a substance which activates a p-opioid receptor.

The u-opioid agonist may be selected from the group including morphine, fentanyl, sufentanil, alfentanil, oxymorphone and hydromorphone inclusive of analogs or derivatives thereof. Preferably, the p-opioid agonist is morphine or an analog or derivative thereof.

For the purposes of this invention, the term "k2-opioid agonist" as used herein refers to selective kappa-opioid receptor agonists wherein the antinociceptive effects thereof are substantially attenuated by, nor-BNI (nor-binaltorphimine; a putatively selective kl/$k_2$-opioid receptor ligand) and wherein the binding of the k, -selective radioligand $^3$H[U69,593] to rat brain membranes is not substantially displaceable by the k2-opioid agonist. Preferably, the k2-opioid agonist is oxycodone.

Of course it will be appreciated that a sub-analgesic dosage of an opioid agonist having dual selectivity for both la and k2 receptors may not be expected to synergize with a sub-analgesic dosage of another p- or k2-opioid agonist because such dual selective ligand may bind to each of the above receptors which may result in lack of occupancy of said other p- or k2, -opioid agonist to its selective receptor.

The term "pharmaceutically acceptable salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

Preferably, the pharmaceutically acceptable salt of oxycodone is a hydrochloride, a terephthalate or a pectinate.

Suitably, the pharmaceutically acceptable salt of morphine is a hydrochloride, a sulphate or a tartrate.

The term "sub-analgesic dosage" as used herein refers to a dosage of a p-opioid agonist solus or a $k_2$-opioid agonist solus which dosage does not result in the production of analgesia when administered to a human or antinociception when administered to a lower animal requiring alleviation of pain. To this extent, it is well known that the lower threshold for an initial dosage of morphine which results in production of analgesia in a naive human adult is 30 mg every four hours administrable by the oral route (Chemy and Portenoy, entitled "Practical Issues In The Management of Cancer Pain," in *Textbook of Cancer Pain*, Third Edition, Eds. Wall and Melzack, Churchill Livingstone) and 4-5 mg every four hours administrable by the intravenous route (Twycross, R. G., entitled "Opioids," in *Textbook of Cancer Pain*, Third Edition, Eds. Wall and Melzack, Churchill Livingstone, pp 943-962). Reference also may be made to an article by Beaver et al. (*J. PharmacoL Exp. Ther.* 207: 92-100 (1978)) that specifies that the lower threshold for an initial dosage of oxycodone resulting in production of analgesia in a naive human adult is 10 mg every four hours administrable by the oral route, although it is recognized that significant variability exists among patients and that significantly higher doses may be needed for some or for even a significant proportion of a typical patient population. Accordingly, the term "sub-analgesic dosage" includes within its scope dosages falling below such lower thresholds. This term will also cover direct administration of the p- or $k_2$-opioid agonist, as well as administration that includes controlled or sustained release of the p- or k2-opioid agonist as described hereinafter. Of course, it will be appreciated that a specific sub-analgesic dosage of a p- or $k_2$-opioid agonist in a particular dosage form, in accordance with the present invention, will be dependent upon the mode or route of administration of the analgesic formulation.

It will be further appreciated by those of skill in the relevant art that the daily dosage required for an individual patient may be administered in immediate release or controlled-release dosage forms. For example, controlled-release dosage forms as described hereinafter may be administered every 12 or 24 hours comprising, respectively, about 3 or 6 times the four hourly dosages disclosed above. In this regard, it is well known that the change from immediate release dosages to controlled release dosages of an opioid is a simple milligram to milligram conversion that results in the same total 'around-the-clock' dose of the opioid (Cherny and Portenoy, "Practical Issues In The Management of Cancer Pain," in *Textbook of Cancer Pain*, Third Edition, Eds. Wall and Melzack, Churchill Livingstone).

With regard to formulating an analgesically effective dose of typical opioid analgesics, it is important to keep in mind the effects of patient variability in response to administration of such analgesic agents. The range of dosages required to produce the desired analgesic effect in an individual patient are recognized to vary considerably from patient to patient as a function of a variety of factors, including disease state. It has been recognized in the art that health care practitioners, in dealing with chronic and/or acute pain, find it necessary to "titrate" appropriate dosages of typical opioid analgesics across a relatively broad range (as much as ten-fold) in order to achieve the desired analgesic affect. Indeed, a series of patents assigned to Euroceltique, S. A., apparently bases the patentability of the disclosed invention on a controlled release oxycodone formulation for once-a-day administration primarily on the capability of the formulation to provide effective analgesia to 90% of potential patients across a four-fold dosage range (10 to 40 mg), the novelty being the much narrower range of dosages. See, for example, U.S. Pat. Nos. 5,508,042 and 5,549,912 (the disclosures of which are specifically incorporated herein by reference).

The present inventors have observed that, in general, it is possible to formulate an analgesically effective dose of a combination of morphine and oxycodone that is approximately 50% of the mass of morphine alone required to produce the desired analgesic effect in an individual patient. As will be apparent to one of skill in the art, a number of advantages accrue from the capacity to provide sufficient analgesia at such low loadings, including a significant reduction in the risk of respiratory complications arising from less desirable side effects of opioid agents. Thus, not only is it possible to formulate a combined oxycodone/morphine analgesic without increasing the risk of adverse effects as evidenced by the onset or exacerbation of respiratory difficulties (see U.S. Pat. No. 6,310,072, the disclosure of which is hereby incorporated specifically by reference), it is actually possible to use such a combined analgesic agent formulation in a therapeutic regimen that significantly reduces the risk of adverse respiratory effects in susceptible patients through the use of formulations with significantly reduced loadings of opioid analgesics. By way of quantitative example, for a given patient, where a total daily dosage required to realize a steady-state level of analgesia may be on the order of 40 mg (for quantitative comparison only), it is possible through the practice of the present invention to provide a combined analgesic product where the total dosage of oxycodone and morphine can be as low as approximately 20 mg, while still providing acceptable steady-state levels of analgesia for that patient. Consistent with the understood meaning of the term "sub-analgesic dosage," such a dosage of morphine alone, administered at a loading of 20 mg, would be insufficient to produce the desired level of analgesia in the specific patient. Further to this principle, where a dosage of morphine alone, at a 20 mg-loading, may be sufficient to produce sufficient analgesia in a given patient, the practice of the present invention provides for achieving a comparable level of analgesia through administration of about 10 mg of a combination of oxycodone and morphine to that patient.

It is also recognized that, in terms of analgesic effect, oxycodone is about 1.5 times more potent (as a function of mass of dose) than morphine. Thus, a sub-analgesic dose for an individual patient can also be defined as about 75% of the amount of the combined mass of morphine and oxycodone relative to the mass of the minimum oxycodone dose required to provide the desired analgesic effect.

According to another aspect of the—invention there is provided a method for producing analgesia in humans and lower animals which comprises administering concurrently to a human or lower animal in need of such treatment a composition comprising a sub-analgesic dosage of a p-opioid agonist suitably in the form of a pharmaceutically acceptable salt and a sub-analgesic dosage of a $k_2$-opioid agonist suitably in the form of a pharmaceutically acceptable salt.

The term "administration concurrently or co-administration" refers to the administration of a single composition containing both p- and $k_2$-optoid agonists, or to the administration of each such opioid agonists as separate compositions and/or delivered by separate routes within a short enough period of time that the effective result is equivalent to that obtained when both such opioid agonists are administered as a single composition.

By "respiratory illness" is meant all disorders, diseases and conditions involving a compromised or impaired respiratory capability including infectious or inflammatory conditions such as asthma, bronchiectasis, pulmonary tuberculosis, chronic obstructive pulmonary disease, bronchitis, bronchopneumonia, chronic laryngitis, chronic sinusitis, emphysema, fibrosing alveolitis, idiopathic pulmonary fibrosis and sarcoidosis. Neoplastic diseases of the lung also are included, for example, non-small cell lung cancer, adenocarcinoma, squamous cell carcinoma, large cell carcinoma, undifferentiated carcinoma, small cell lung cancer, oat cell cancer and mesothelioma. Also included as respiratory illnesses are sleep apneas that are classified into three types: central, obstructive, and mixed. In central sleep apnea the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea. The most common type of apnea is obstructive sleep apnea.

By "pharmaceutically-acceptable carrier" is meant a solid or liquid filler, diluent or encapsulating substance which may be safely used in systemic administration.

Pharmaceutical compositions of the present invention suitable for oral or parenteral administration may be presented as discrete units such as capsules, sachets or tablets each containing a pre-determined amount of each of the strong opioids, as a powder or granules or as a solution or a suspension in an aqueous liquid, a non-aqueous liquid, an oil-inwater emulsion or a water-in-oil liquid emulsion. Such compositions may be prepared by any of the methods of pharmacy but all methods include the step of bringing into association the sub-analgesic dosages of each of the strong opioids as described above with the carrier that constitutes one or more necessary ingredients. In general, the compositions are prepared by uniformly and intimately admixing the strong opioids with liquid carriers or finely divided solid carriers or both, and then, if necessary, shaping the product into the desired presentation.

The opiate compounds (also referred to herein as "active compounds") useful in the methods of the invention can be incorporated into pharmaceutical compositions suitable for administration to human patients. Such compositions typically comprise the active compounds and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. As discussed above, supplementary active compounds can also be incorporated into the compositions A pharmaceutical composition of the invention is formulated to be compatible with its intended route of administration. Examples of routes of administration include, but are not limited to, parenteral, e.g., intravenous, intradermal, subcutaneous, oral, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The composition preferably is sterile and should be fluid to the extent that easy syringability exists. The compositions suitably should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in a therapeutically effective or beneficial amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. Suitable oral compositions may be, e.g., enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer. Alternatively, the compositions of the present invention may also be formulated into suitable compositions for pulmonary delivery via dry powder inhalers.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosages for use in humans. The dosage of such compounds lies preferably within a range of circulating concentrations that include the $ED_{50}$ with little or no toxicity: The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $1C_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions (e.g., written) for administration, particularly such instructions for use of the active agent to treat against pain incurred as a result of any disorder, disease, trauma or pen-operative care.

The present invention will be more specifically explained in the following examples. However, it should be understood that the following examples are intended to illustrate the present invention but not in any manner to limit the scope of the present invention. All documents mentioned herein are incorporated herein by reference in their entirety.

EXAMPLES

Example 1

Effects of Combined Morphine/Oxycodone Formulations on Respiration

Objective The main objective was to compare the ventilatory responses to hypoxia and hypercarbia following one hour intravenous infusions of (1) morphine 15 mg, or (2) oxycodone 15 mg, or (3) morphine 10 mg+oxycodone 5 mg, or (4) oxycodone 10 mg+morphine 5 mg, or (5) morphine 7.5 mg+oxycodone 7.5 mg. Each infusion was administered over 1 h and was designated by its respective composition as M15, M10_05, M7.5_07.5, M5_010 or 015.

Design A triple blind placebo-controlled, 5-period, randomised crossover study in 10 males was conducted. On each of the 5 study days for each of the 10 subjects, there was a baseline period, followed by either a 1 h drug or "placebo" i.v. infusion, followed by 1 h "placebo" or drug infusion, followed by a 1 h "washout". Serial measures of drug effect were accompanied by serial peripheral venous blood sampling. The hypoxemic and hypercapnic ventilatory responses were determined by subjects breathing hypoxemic and hypercapnic gas mixtures. The changed gases for making the hypercapnic and hypoxaemic states were breathed by the subject from a specially constructed anaesthetic apparatus that had been modified to allow the high flow rates required for calibrating the pneumotachography apparatus. The gases were stored in pre-measured concentrations in large bags (weather balloons) to act as Douglas bags for fresh gas reservoirs as a "demand valve" system. Carbon dioxide enriched gas was delivered in this manner. Hypoxic gas mixtures were also delivered into a reservoir balloon but during the subject's breathing of this mixture to enable changes to be made to gas concentrations in response to observed $SpO_2$.

Analysis of variance (ANOVA) was first performed on the baseline data in comparison to the three serial measures during the "placebo" infusion if this was administered first. No systematic differences were found, so the data were melded into a "control" data set for assignment as "before" drug administration. With the data re-organized into "before", "during" and "after" drug administration periods, the statistical analysis proceeded in stages.

Interactive effect of drugs on respiration Although ventilatory effects of all the test articles were found, no unexpected or disproportionate effects of any of the tested combinations of morphine and oxycodone were found. It was therefore concluded that there was no synergism between the drugs on the extent of depression of respiration.

Effect of plasma level of drug on respiration The results of individual subjects were examined for the effect of the blood level of the combined plasma level of drug vs. minute ventilation (the volume of air per minute moved into or out of the lung). The results shown in FIG. 1 are in accord with the invention that as blood level of drug is increased, minute ventilation decreases.

Example 2

Analgesia in Patients using Sub-Analgesic Combinations of Morphine & Oxycodone in a Ratio of 1:0.66 by Weight Objective: to determine the dose of a taste masked oral syrup of morphine and oxycodone in a ratio of 1:0.66 by weight compared to a taste masked syrup containing morphine alone.

Design: A triple-blind (patient, investigator and analyst) randomized, controlled, two-period cross-over study was designed to assess the effectiveness of morphine compared to an oxycodone and morphine mixture. The study was carried out in 21 patients with chronic non-cancer pain. The morphine was formulated to a solution concentration of 5 mg/mL and the combination formulation to a concentration of morphine 1.5 mg/mL and oxycodone 1 mg/mL. The solution strengths were determined so that the expected total dose per day in mL would be similar between the two treatments thereby retaining blinding. Each opioid solution was administered every 4 hours with the 10 pm and 2 am doses being combined to provide 5 doses per day. The exact number of mL of each solution was recorded at each dose. Rescue doses were allowed as required. The total daily dose (regular plus rescue doses) was calculated for each day and the next day's total regular dose was set to this amount (divided into 6 equal dose amounts). The dose was titrated based on visual analogue scale (VAS) pain scores and tolerability. When the dose remained stable (±10%) for three days steady-state was assumed and a pharmacokinetic study was undertaken, and then the treatment was stopped for that patient. The patient was then changed immediately to the alternative opioid treatment and the study repeated, including the pharmacokinetic study.

Results: VAS In all patients, steady-state was achieved with both formulations. There was no significant difference between the pre-treatment VAS and steady-state VAS for the oxycodone/morphine combination (P=0.46). For the morphine formulation the pre-treatment VAS was statistically significantly greater than the steady-state VAS (P=0.033), but the difference mean of 1.2 cm is of borderline clinical significance. In addition the pre-treatment VAS for period I was statistically significantly greater than the steady-state VAS for this period (P=0.029)—however this difference of 8% did not reach clinical significance. There was no difference due to treatment order. Analysis of covariance for treatment adjusting for period and order effects, did not reveal a significant difference (P=0.16).

Results: Analgesic Effect The effective dose of the 1:0.66 combination versus morphine required to provide analgesia is shown in Table 1. The results show a weight of the combined product to weight of morphine to be 51%. This results was statistically significant (P<0.001).

TABLE 1

Comparison of doses required for stabilized pain control.

| Treatment | Patients | Dose, mg (by weight) |
|---|---|---|
| Morphine | 21 | 108 |
| Combination of morphine to oxycodone 1:0.66 | 21 | 55 |
| (Morphine + Oxycodone dose)/Morphine dose | | 51% |

Example 3

Analgesia in Patients using Sub-Analgesic Combinations of Morphine & Oxycodeone in a Ratio of 1:2.0 by Weight Objective: to determine the dose of a taste masked oral syrup of morphine and oxycodeone in a ratio of 1:2.0 by weight compared to a taste masked syrup containing morphine alone.

Design & Analysis: a similar design and analysis to that used in Example I was followed.

Results: Analgesic Effects As with Example 2, no significant differences in VAS scores were noted between any of the treatment groups. The effective dose of the 1:2.0 combination versus morphine required to provide analgesia is shown in Table 2. The results show a weight of the combined product to weight or morphine to be 46%. The results was statistically significant (P<0.002).

TABLE 2

Comparison of doses required for stabilized pain control.

| Treatment | Patients | Dose, mg (by weight) |
|---|---|---|
| Morphine | 22 | 68 |
| Combination of morphine to oxycodone 1:2.0 | 21 | 55 |
| (Morphine + Oxycodone dose)/Morphine dose | | 46% |

In summary, the combined results of the three examples indicates that as the dose of morphine and oxycodone is decreased to give lower plasma levels, the extent of respiration depression decreases. Further, that doses of combinations of morphine and oxycodone in the ratios of about 1 to 0.66 by weight of about 1 to 2.0 by weight provide analgesia when administered at 50% of the minimum dose of morphine required to give analgesia in humans. Thus, combinations of sub-analgesic doses ff morphine and oxycodeone produce decreased depression of respiration and, thus, represent a safer product than morphine alone.

I claim:

1. A method of treating a human in need thereof for the alleviation or prevention of pain, said method comprising co-administering to the human:
    an oral sub-analgesic dose of a pharmaceutically acceptable salt of morphine, wherein the pharmaceutically acceptable salt is a sulphate salt or a hydrochloride salt; and
    (ii) an oral sub-analgesic dose of a pharmaceutically acceptable salt of oxycodone, wherein the pharmaceutically acceptable salt is a hydrochloride salt;
    wherein the pharmaceutically acceptable salt of morphine and the pharmaceutically acceptable salt of oxycodone are in a ratio of about 1:0.66 by weight, and wherein the method produces an analgesic effect in the human.

2. The method of claim 1, wherein the pharmaceutically acceptable salt of morphine is the sulphate salt.

3. The method of claim 1, wherein the oral sub-analgesic dose of a pharmaceutically acceptable salt of morphine and the oral sub-analgesic dose of a pharmaceutically acceptable salt of oxycodone are co-administered in separate compositions.

4. The method of claim 1, wherein the oral sub-analgesic dose of a pharmaceutically acceptable salt of morphine and the oral sub-analgesic dose of a pharmaceutically acceptable salt of oxycodone are co-administered in a single composition.

5. The method of claim 1, wherein the oral sub-analgesic dose of a pharmaceutically acceptable salt of morphine and the oral sub-analgesic dose of a pharmaceutically acceptable salt of oxycodone are admixed with one or more liquid carriers.

6. The method of claim 1, wherein the oral sub-analgesic dose of a pharmaceutically acceptable salt of morphine and the oral sub-analgesic dose of a pharmaceutically acceptable salt of oxycodone are admixed with one or more solid carriers.

7. The method of claim 6, wherein the admixture of the oral sub-analgesic dose of a pharmaceutically acceptable salt of morphine, the oral sub-analgesic dose of a pharmaceutically acceptable salt of oxycodone and the one or more solid carriers are shaped into one or more tablets.

8. The method of claim 1, wherein the oral sub-analgesic dose of a pharmaceutically acceptable salt of morphine and the oral sub-analgesic dose of a pharmaceutically acceptable salt of oxycodone are co-administered in immediate release dosage form.

9. The method of claim 1, wherein the oral sub-analgesic dose of a pharmaceutically acceptable salt of morphine and the oral sub-analgesic dose of a pharmaceutically acceptable salt of oxycodone are co-administered in sustained release dosage form.

10. The method of claim 1, wherein the oral sub-analgesic dose of a pharmaceutically acceptable salt of morphine and the oral sub-analgesic dose of a pharmaceutically acceptable salt of oxycodone are co-administered in controlled release dosage form.

11. The method of claim 1, wherein the oral sub-analgesic dose of a pharmaceutically acceptable salt of morphine is in a quantity of about 3 mg; and the oral sub-analgesic dose of a pharmaceutically acceptable salt of oxycodone is in a quantity of about 2 mg.

12. The method of claim 1, wherein the oral sub-analgesic dose of a pharmaceutically acceptable salt of morphine is in a quantity of about 6 mg; and the oral sub-analgesic dose of a pharmaceutically acceptable salt of oxycodone is in a quantity of about 4 mg.

13. The method of claim 1, wherein the oral sub-analgesic dose of a pharmaceutically acceptable salt of morphine is in a quantity of about 9 mg; and the oral sub-analgesic dose of a pharmaceutically acceptable salt of oxycodone is in a quantity of about 6 mg.

14. The method of claim 1, wherein the oral sub-analgesic dose of a pharmaceutically acceptable salt of morphine is in a quantity of about 12 mg; and the oral sub-analgesic dose of a pharmaceutically acceptable salt of oxycodone is in a quantity of about 8 mg.

15. The method of claim 1, wherein the oral sub-analgesic dose of a pharmaceutically acceptable salt of morphine is in a quantity of about 15 mg; and the oral sub-analgesic dose of a pharmaceutically acceptable salt of oxycodone is in a quantity of about 10 mg.

16. A method of treating a human in need thereof for the alleviation or prevention of pain, said method comprising co-administering to the human a solid, oral, immediate release capsule comprising a combination of a sub-analgesic dose of morphine sulphate and a sub-analgesic dose of oxycodone hydrochloride in a ratio of about 1:0.66 by weight, wherein the method produces an analgesic effect in the human.

* * * * *